(12) United States Patent
Tawwater et al.

(10) Patent No.: US 11,786,810 B2
(45) Date of Patent: Oct. 17, 2023

(54) TWO-ENVIRONMENT GAME PLAY SYSTEM

(71) Applicant: FlyingTee Tech, LLC, Tulsa, OK (US)

(72) Inventors: Ryan Tawwater, Oklahoma City, OK (US); John Vollbrecht, Oklahoma City, OK (US); James Vollbrecht, Dallas, TX (US)

(73) Assignee: FlyingTee Tech, LLC, Tulsa, OK (US)

( * ) Notice: Subject to any disclaimer, the term of this patent is extended or adjusted under 35 U.S.C. 154(b) by 94 days.

(21) Appl. No.: 17/338,839

(22) Filed: Jun. 4, 2021

(65) Prior Publication Data

US 2021/0291040 A1 Sep. 23, 2021

Related U.S. Application Data

(63) Continuation of application No. 14/819,999, filed on Aug. 6, 2015, now Pat. No. 11,027,193, which is a
(Continued)

(51) Int. Cl.
*A63F 13/245* (2014.01)
*A63B 69/36* (2006.01)
(Continued)

(52) U.S. Cl.
CPC ........ *A63F 13/245* (2014.09); *A63B 24/0003* (2013.01); *A63B 24/0021* (2013.01);
(Continued)

(58) Field of Classification Search
CPC ............ A63B 69/3691; A63B 24/0021; A63B 24/0003; A63B 2102/32;
(Continued)

(56) References Cited

U.S. PATENT DOCUMENTS

| 4,137,566 A | 1/1979 | Haas et al. |
| 4,192,510 A | 3/1980 | Miller |

(Continued)

FOREIGN PATENT DOCUMENTS

| CA | 2839362 A1 | 10/2012 |
| CN | 1120964 A | 4/1996 |

(Continued)

OTHER PUBLICATIONS

"Examination Report—94(3) for European Application No. 14819897.1 dated Mar. 10, 2023".
(Continued)

*Primary Examiner* — Jeffrey S Vanderveen
(74) *Attorney, Agent, or Firm* — Crowe & Dunlevy, P.C.

(57) ABSTRACT

A game-play environment includes a tee box, a range surface, and a monitor. The tee box is configured to permit a player to hit a golf ball onto the range surface. The range surface has a plurality of physical markers. The monitor depicts a virtual environment that includes a plurality of virtual components. Some of the virtual components are visual cues that correspond to the physical markers. A player can play the game by targeting the appropriate physical marker that corresponds to the desired visual cue.

25 Claims, 11 Drawing Sheets

Related U.S. Application Data continuation-in-part of application No. 14/321,333, filed on Jul. 1, 2014, now abandoned.

(60) Provisional application No. 61/841,544, filed on Jul. 1, 2013.

(51) Int. Cl.
*A63B 24/00* (2006.01)
*A63F 13/98* (2014.01)
*A63F 13/573* (2014.01)
*G16H 20/30* (2018.01)
*A63B 102/32* (2015.01)

(52) U.S. Cl.
CPC ........ *A63B 69/3691* (2013.01); *A63F 13/573* (2014.09); *A63F 13/98* (2014.09); *G16H 20/30* (2018.01); *A63B 2024/0031* (2013.01); *A63B 2102/32* (2015.10); *A63B 2220/05* (2013.01); *A63B 2220/803* (2013.01)

(58) Field of Classification Search
CPC ...... A63B 2024/0031; A63B 2220/803; A63B 2220/05; A63F 13/98; A63F 13/245; A63F 13/573; G16H 20/30
See application file for complete search history.

(56) References Cited

U.S. PATENT DOCUMENTS

| | | | |
|---|---|---|---|
| 4,283,056 A * | 8/1981 | Miller | A63B 69/36 473/409 |
| 4,673,183 A | 6/1987 | Trahan | |
| 5,092,602 A | 3/1992 | Witler et al. | |
| 5,150,895 A | 9/1992 | Berger | |
| 5,246,232 A | 9/1993 | Eccher et al. | |
| 5,290,037 A | 3/1994 | Witler et al. | |
| 5,303,924 A * | 4/1994 | Kluttz | A63B 69/3658 473/409 |
| 5,342,051 A | 8/1994 | Rankin et al. | |
| 5,375,832 A | 12/1994 | Witler et al. | |
| 5,398,936 A | 3/1995 | Kluttz et al. | |
| 5,401,026 A | 3/1995 | Eccher et al. | |
| 5,413,345 A | 5/1995 | Nauck | |
| 5,486,002 A | 1/1996 | Witler et al. | |
| 5,489,099 A | 2/1996 | Rankin et al. | |
| 5,653,642 A | 8/1997 | Bonacorsi | |
| 5,700,204 A | 12/1997 | Teder | |
| 5,743,815 A | 4/1998 | Helderman | |
| 5,820,496 A | 10/1998 | Bergeron | |
| 5,879,246 A | 3/1999 | Gebhardt et al. | |
| 6,012,987 A | 1/2000 | Nation | |
| 6,179,720 B1 | 1/2001 | Rankin et al. | |
| 6,217,444 B1 | 4/2001 | Kataoka et al. | |
| 6,304,665 B1 | 10/2001 | Cavallaro et al. | |
| 6,320,173 B1 | 11/2001 | Vock et al. | |
| 6,322,455 B1 | 11/2001 | Howey | |
| 6,371,862 B1 | 4/2002 | Reda | |
| 6,373,508 B1 | 4/2002 | Moengen | |
| 6,409,607 B1 | 6/2002 | Libit et al. | |
| 6,437,559 B1 | 8/2002 | Zajac et al. | |
| 6,520,864 B1 | 2/2003 | Wilk | |
| 6,547,671 B1 | 4/2003 | Mihran | |
| 6,607,123 B1 | 8/2003 | Jollifee et al. | |
| 6,702,292 B2 | 3/2004 | Takowsky | |
| 6,764,412 B2 | 7/2004 | Gobush et al. | |
| 6,781,621 B1 | 8/2004 | Gobush et al. | |
| 6,898,971 B2 | 5/2005 | Dilz | |
| 6,905,339 B2 | 6/2005 | DiMare et al. | |
| 6,974,391 B2 | 12/2005 | Ainsworth et al. | |
| 6,998,965 B1 | 2/2006 | Luciano et al. | |
| 7,040,998 B2 | 5/2006 | Jolliffe et al. | |
| 7,052,391 B1 | 5/2006 | Luciano | |
| 7,059,974 B1 | 6/2006 | Jolliffe et al. | |
| 7,095,312 B2 | 8/2006 | Erario et al. | |
| 7,143,639 B2 | 12/2006 | Gobush | |
| 7,160,196 B2 | 1/2007 | Thirkettle et al. | |
| 7,214,138 B1 | 5/2007 | Stivers et al. | |
| 7,223,169 B2 | 5/2007 | Imaeda et al. | |
| 7,317,388 B2 | 1/2008 | Kawabe et al. | |
| 7,321,330 B2 | 1/2008 | Sajima | |
| 7,337,965 B2 | 3/2008 | Thirkettle et al. | |
| 7,344,446 B2 | 3/2008 | Wyeth | |
| 7,497,780 B2 | 3/2009 | Kiraly | |
| 7,641,565 B2 | 1/2010 | Kiraly | |
| 7,787,886 B2 | 8/2010 | Markhovsky et al. | |
| 7,815,516 B1 | 10/2010 | Mortimer et al. | |
| 7,822,424 B2 | 10/2010 | Markhovsky et al. | |
| 7,837,572 B2 | 11/2010 | Bissonnette et al. | |
| 7,843,429 B2 | 11/2010 | Pryor | |
| 7,854,669 B2 * | 12/2010 | Marty | A63B 24/0021 473/448 |
| 8,018,375 B1 | 9/2011 | Alexopoulos et al. | |
| 8,068,095 B2 | 11/2011 | Pryor | |
| 8,077,917 B2 | 12/2011 | Forsgren | |
| 8,113,964 B2 | 2/2012 | Lindsay | |
| 8,142,302 B2 | 3/2012 | Balardeta et al. | |
| 8,257,189 B2 | 9/2012 | Koudele et al. | |
| 8,328,653 B2 | 12/2012 | Lock | |
| 8,335,345 B2 | 12/2012 | White et al. | |
| 8,400,346 B2 | 3/2013 | Hubbard et al. | |
| 8,409,024 B2 | 4/2013 | Marty et al. | |
| 2005/0227792 A1 | 10/2005 | McCreary et al. | |
| 2007/0078018 A1 | 4/2007 | Kellogg et al. | |
| 2007/0293331 A1 | 12/2007 | Tuxen | |
| 2008/0139330 A1 | 6/2008 | Tuxen | |
| 2008/0182685 A1 | 7/2008 | Marty et al. | |
| 2008/0261711 A1 | 10/2008 | Tuxen | |
| 2009/0036237 A1 | 2/2009 | Nipper et al. | |
| 2009/0295624 A1 | 12/2009 | Tuxen | |
| 2010/0137079 A1 | 6/2010 | Burke et al. | |
| 2011/0077093 A1 * | 3/2011 | Garratt | A63B 69/3658 473/131 |
| 2011/0230986 A1 | 9/2011 | Lafortune et al. | |
| 2011/0286632 A1 | 11/2011 | Tuxen et al. | |
| 2012/0068879 A1 | 3/2012 | Tuxen | |
| 2013/0039538 A1 | 2/2013 | Johnson et al. | |
| 2013/0084930 A1 | 4/2013 | Chang et al. | |
| 2013/0274025 A1 | 10/2013 | Luciano et al. | |
| 2016/0287967 A1 | 10/2016 | Baldwin et al. | |

FOREIGN PATENT DOCUMENTS

| | | |
|---|---|---|
| CN | 1556721 A | 12/2004 |
| KR | 101078898 B1 | 11/2011 |
| WO | 03022369 A3 | 10/2003 |
| WO | 2007037705 A1 | 4/2007 |
| WO | 2011065804 A2 | 6/2011 |
| WO | 2012134208 A2 | 10/2012 |

OTHER PUBLICATIONS

"Examination Report—94(3) for European Application No. 14819897.1 dated Dec. 16, 2021".
"Examination Report—94(3) for European Application No. 14819897.1 dated Jun. 4, 2020".
"Examination Report—94(3) for European Application No. 14819897.1 dated Oct. 8, 2018".
"Examination Report in UAE Application No. P1722/2015 dated Mar. 17, 2021".
"Examination report No. 1 for Australian Patent Application No. 2014284410 dated Mar. 2, 2019".
"Examination report No. 1 for Australian Patent Application No. 2020201531 dated Dec. 2, 2020".
"Examination report No. 2 for Australian Patent Application No. 2020201531 dated Nov. 24, 2021".
"Examiner's Requisition for Canadian Patent Application No. 2916462 dated Jun. 2, 2021".
"Final Office Action for Japanese Patent Application No. 2021-022027 dated Jul. 25, 2022".

(56) References Cited

OTHER PUBLICATIONS

"First Examination Report for India Patent Application No. 11509/DELNP/2015 dated Sep. 9, 2019".
"First Office Action for Chinese Patent Application No. 201480037296.2 dated Feb. 14, 2017".
"First Office Action for Chinese Patent Application No. 201811316634.2 dated Jun. 25, 2021".
"First Office Action for Japanese Patent Application No. 2016-524324 dated May 28, 2018".
"First Office Action for Japanese Patent Application No. 2019-000502 dated Mar. 9, 2020".
"First Office Action for Japanese Patent Application No. 2021-022027 dated Feb. 2, 2022".
"Office Action for Canadian Patent Application No. 2916462 dated Jul. 21, 2021".
"Search and Examination Report in UAE Application No. P1722/2015".
"Second Office Action for Chinese Patent Application No. 201480037296.2 dated Jul. 10, 2017".
"Second Office Action for Chinese Patent Application No. 201811316634.2 dated Feb. 23, 2022".
"Second Office Action for Japanese Patent Application No. 2019-000502 dated Sep. 23, 2020".
"Supplementary European Search Report for European Patent Application No. 14819897.1 dated Jan. 20, 2017".
"Third Office Action for Chinese Patent Application No. 201480037296.2 dated Dec. 29, 2017".

\* cited by examiner

TWO-ENVIRONMENT GAME PLAY SYSTEM

CROSS REFERENCE TO RELATED APPLICATIONS

This application is a continuation of and claims priority to U.S. patent application Ser. No. 14/819,999, filed Aug. 6, 2015, now U.S. Pat. No. 11,027,193, issued Jun. 8, 2021, which claims priority to and is a continuation-in-part of, U.S. patent application Ser. No. 14/321,333, filed on Jul. 1, 2014, which claims the benefit of U.S. Provisional Patent Application No. 61/841,544, filed on Jul. 1, 2013. This application incorporates each of the foregoing applications by reference in its entirety into this document as if fully set out at this point.

BACKGROUND OF THE INVENTION

1. Field of the Invention

This invention relates to a system and method related to a game play environment.

2. Description of the Related Art

Conventional methods of tracking an object (e.g., golf ball, basketball, baseball, etc.) employ various types of sensors including Doppler radar technology, camera-based technology, high speed 3D camera-based technology, and stereoscopic sensors. The sensors can be configured to track the object and with the aid of a computer can recreate the movement of the object in a computerized virtual environment. In athletic application, these tracking systems have been used to provide feedback for coaching, player development, and other training/improvement applications, with focus on the movement of a virtual object relative to a virtual environment. The prior art is principally focused on providing analysis about the player's technique and the resulting effect on the flight path of the object. These systems have found a particular benefit in the area of golf instruction.

Conventional indoor golf simulators utilize sensors, as mentioned above, to represent data points in a virtual space, which are projected onto a screen into which the golf ball is hit. Such simulators monitor the initial flight of the ball with sensors, which extrapolate the full flight of the ball and relay those data points to a computer system that creates a representation of the data points in a virtual space, such as a virtualized hole on a golf course. The prior art focuses on capturing the data points and incorporating the data points into a predominately virtual environment, with no identifiable links to the physical environment where the golf ball was actually hit.

It is apparent that there is a need for a system and method of tracking a ball, or other object, and rendering the flight path of that ball in a virtual gaming environment that is coordinated with the physical environment in which the ball is struck as well as providing games and results based on various targets within the physical or virtual environment. Additionally, there is the need to alter the game play environment that the user experiences without changing the physical environment into which the ball or object is hit and to use sensors to track the entire flight of the ball in the actual physical environment. The present invention is focused on solving such a need and providing the techniques thereby to fulfil these needs.

Before proceeding to a detailed description of the invention, however, it should be noted and remembered that the description of the invention which follows, together with the accompanying drawings, should not be construed as limiting the invention to the examples (or embodiments) shown and described. This is so because those skilled in the art to which the invention pertains will be able to devise other forms of this invention within the ambit of the appended claims.

SUMMARY OF THE INVENTION

Described herein is a game-play environment that includes a tee box, a range surface, and a monitor. The tee box is configured to allow a player to hit a golf ball onto the range surface. The range surface has a plurality of physical markers. The monitor is positioned so that the player can see the monitor while in the tee box. The monitor depicts a virtual environment that corresponds to a desired virtual game. Depending on the particular game selected, a set of virtual components are displayed on the monitor. Some of these virtual components are visual cues that correspond to the physical markers on the range surface. The player can achieve the game's objectives by targeting the appropriate physical marker that corresponds to the desired visual cue.

The foregoing has outlined in broad terms some of the more important features of the invention disclosed herein so that the detailed description that follows may be more clearly understood, and so that the contribution of the named inventors to the art may be better appreciated. The invention is not to be limited in its application to the details of the construction and to the arrangements of the components set forth in the following description or illustrated in the drawings. Rather, the invention is capable of other embodiments and of being practiced and carried out in various other ways not specifically enumerated herein. Finally, it should be understood that the phraseology and terminology employed herein are for the purpose of description and should not be regarded as limiting, unless the specification specifically so limits the invention.

BRIEF DESCRIPTION OF THE DRAWINGS

These and further aspects of the invention are described in detail in the following examples and accompanying drawings.

DETAILED DESCRIPTION OF THE INVENTION

Figure 1:
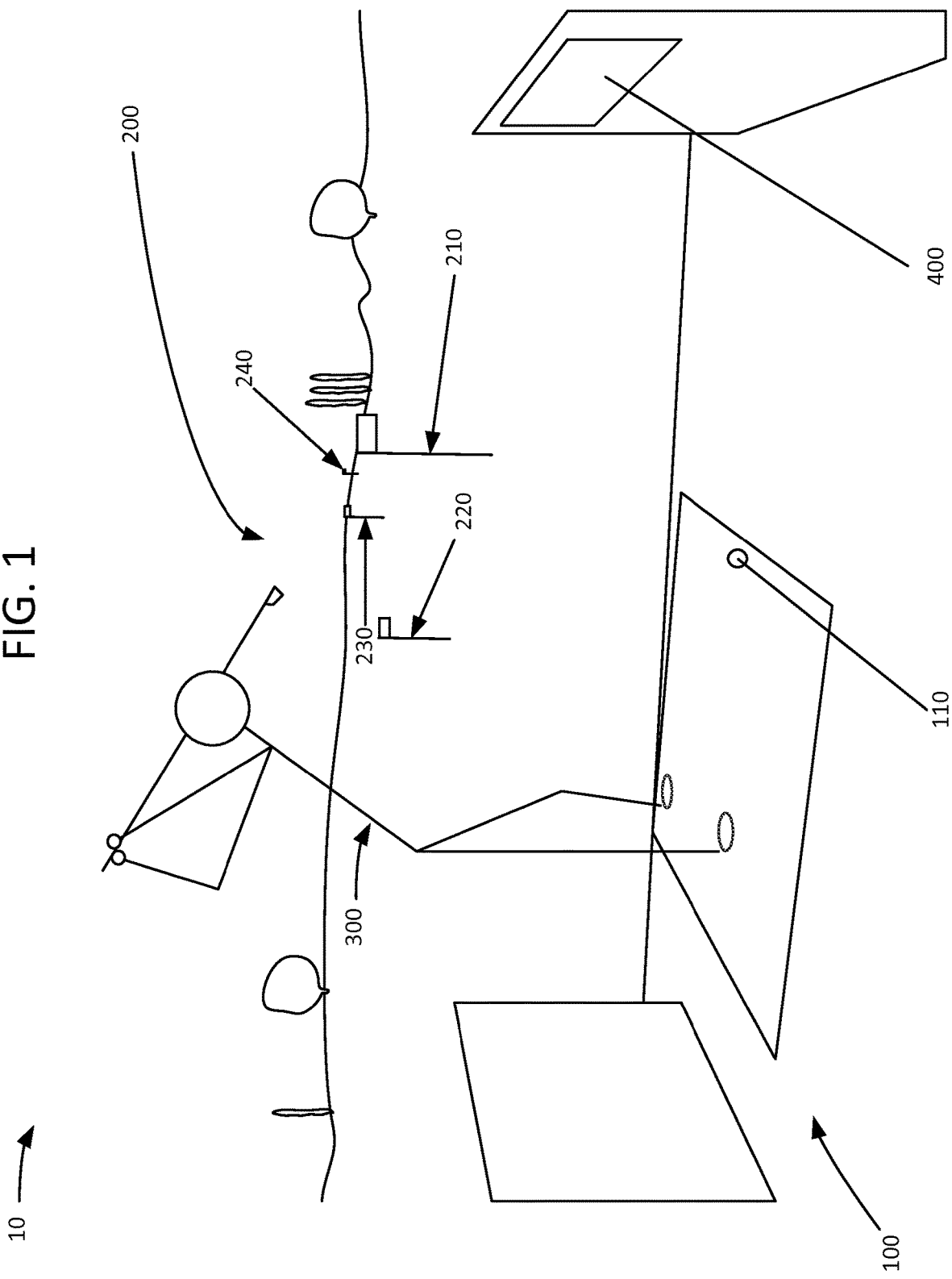
FIG. 1 depicts a perspective view of a physical environment that is used in the game play.

While this invention is susceptible of embodiment in many different forms, there is shown in the drawings, and will herein be described hereinafter in detail, some specific embodiments of the invention. It should be understood, however, that the present disclosure is to be considered an exemplification of the principles of the invention and is not intended to limit the invention to the specific embodiments so described.

In accordance with an illustrative embodiment of the invention, a game-play environment 10 includes a tee box 100 and a range surface 200. The tee box 100 includes a ball 110 and a monitor 400. The range surface 200 includes a plurality of physical markers 210, 220, 230, and 240. FIG. 1 is a perspective view of the game-play environment 10. Shown therein is a player 300 positioned in the tee box 100 over the golf ball 110 and facing the monitor 400. It is understood that the particular position of the player 300 within the tee box 100 enables that player 300 to see the physical markers 210, 220, 230, and 240 and also to see the monitor 400. It will be further understood that while FIG. 1 depicts the game-play environment 10, other embodiments and arrangements of the constituent parts of the game-play environment 10 are possible. For example, the monitor 400 can be raised or mounted on a standard pivot mount for adjustable positioning within the tee box 100. Similarly, the positioning of the plurality of physical markers on the range surface 200 can be adjusted as desired for a particular embodiment. The plurality of physical markers may generally be distributed throughout the range surface 200 to facilitate game play, as discussed below. The physical markers are distributed throughout the range surface 200 at distances of approximately 60 yards, 130 yards, 180 yards, and 210 yards from the tee box 100.

Figure 2:
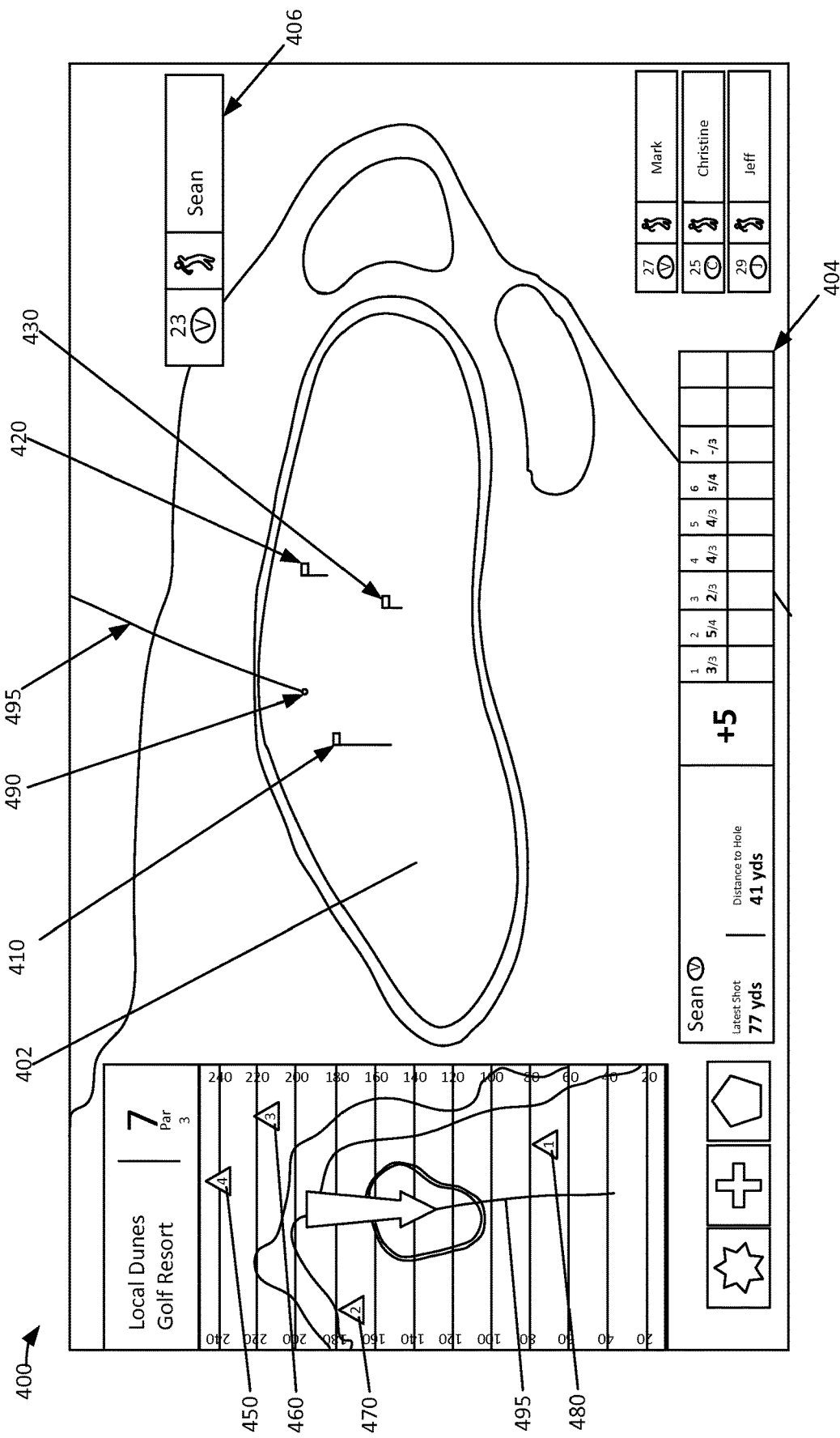
FIG. 2 depicts a side perspective view of a virtual environment showing the path a ball travels through that virtual environment.

Turning to FIG. 2, depicted therein is a virtual environment that is displayed to the player 300 on the monitor 400. The virtual environment 10 is configured to play a virtual game of golf. Accordingly, the virtual environment shown in FIG. 2 consists of a plurality of visual components appropriate for a golf game, including without limitation, a golf green 402, a player score card 404, a current player information box 406, a plurality of player location flags 410, 420, and 430, a plurality of visual cues 450, 460, 470, and 480, a virtual golf ball 490, and a golf ball flight path 495.

Some of these visual components correspond with physical aspects of the range surface 200 and tee box 100. For example, the visual cues 450, 460, 470, and 480 correspond with the physical markers 210, 220, 230, and 240 respectively. Importantly, the relative positions and distances between the physical markers 210, 220, 230, and 240 are the same relative positions and distances depicted between the visual cues 450, 460, 470, and 480. It will be understood that by depicting a plurality of visual cues in the virtual environment that correspond to a plurality of physical markers on the range surface 200, various desirable features of the golf game become possible. It will be further understood that other games can benefit from the correspondence of physical markers with visual cues, including without limitation baseball, football, ultimate frisbee, tennis, and others.

One such benefit is that after a player 300 strikes the golf ball 110, the place that the golf ball 110 comes to rest on the range surface 200 can be depicted within the virtual environment as being in a position and distance from each of the plurality of visual cues that corresponds to position and distance of the golf ball 110 from each of the plurality of physical markers on the range surface. For example, if the resting place of the golf ball 110 is 10 feet north of physical marker 220, 15 feet west of physical marker 230, and 40 feet south of physical marker 240, the monitor 400 will display a virtual golf ball 490 as being 10 feet north of visual cue 450, 15 feet west of visual cue 460, and 40 feet south of 470.

Another benefit of depicting a plurality of visual cues in the virtual environment that correspond to a plurality of physical markers on the range surface 200, is that the actual path that the golf ball 110 travels from the tee box 110 to the range surface 200 can be depicted within the virtual environment and displayed on the monitor 400. FIG. 2 depicts this path 495.

Yet another benefit of depicting a plurality of visual cues in the virtual environment that correspond to a plurality of physical markers on the range surface 200 is that the player 300 can use the plurality of physical markers as targets that correspond to particular visual components depicted within the virtual environment. For example turning to FIG. 4*a*, if in the particular game being played in the game-play environment 10 it is desirable to get the virtual golf ball 490 to rest near visual component 498 (which his depicted as the cup on a golf hole), then the player 300 can adjust his golf shot (by changing golf clubs, stroke mechanics, foot position, body position, etc.) to improve the chances that the golf ball 110 will come to rest near physical marker 210, which corresponds to visual cue 450, the visual cue closest to visual component 498.

Figure 4C:
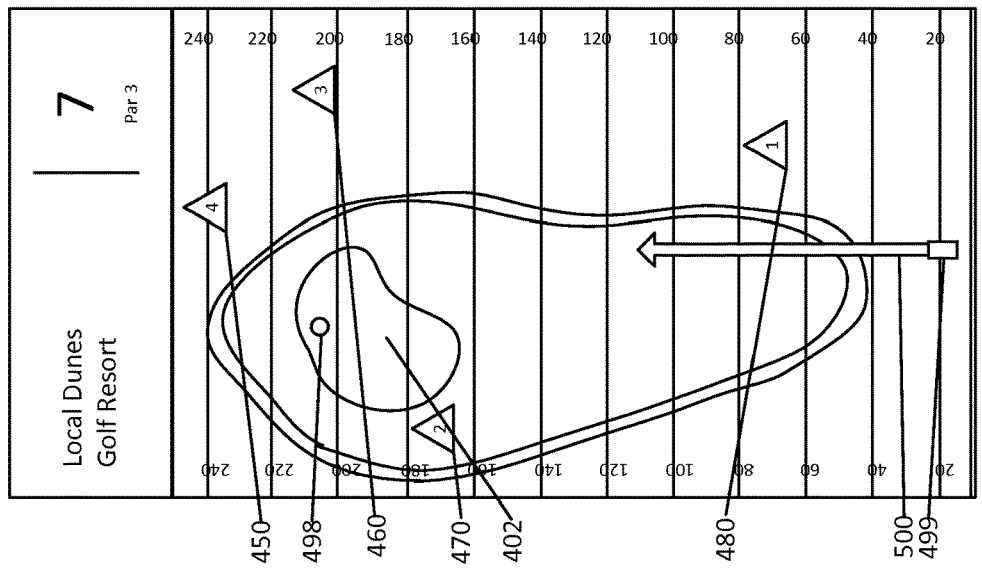
FIG. 4c depicts a top view from FIGS. 4a and 4b wherein the virtual environment has been further adjusted for aiming.
Figure 4B:
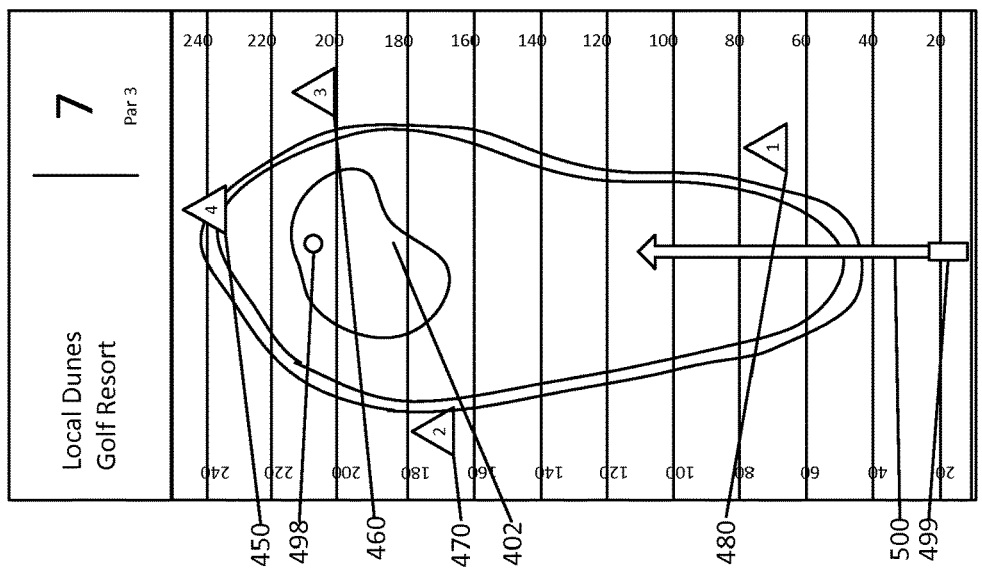
FIG. 4b depicts a top view from FIG. 4a wherein the virtual environment has been adjusted for aiming.
Figure 4A:
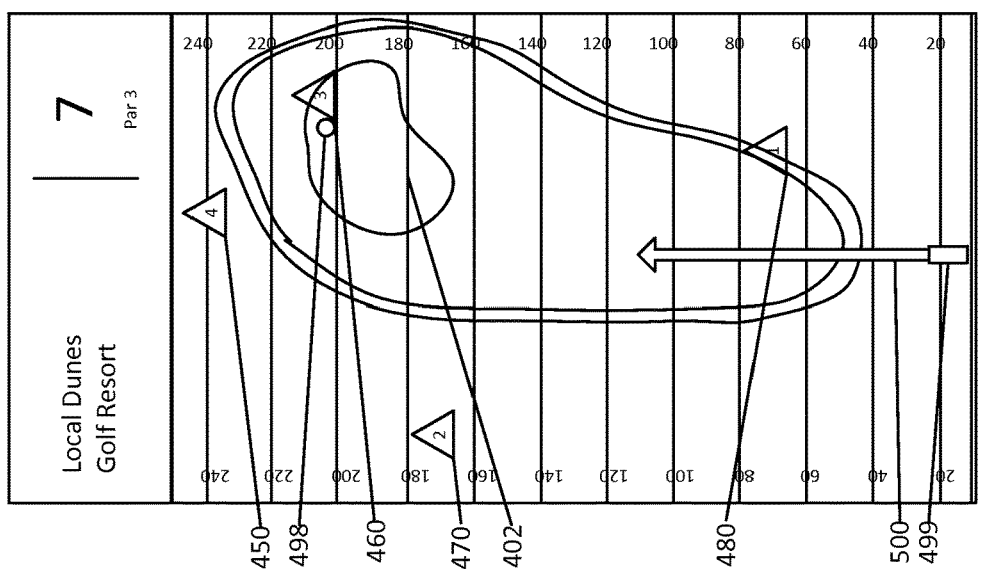
FIG. 4a depicts a top view of a virtual environment.

It will be understood that the virtual environment may also be adjusted so that the visual cues 450, 460, 470, and 480 that correspond to physical markers 210, 220, 230, and 240 are better aligned with the desired visual components. For example, FIG. 4*b* depicts the same virtual environment of FIG. 4*a*, except that the perspective has been selectively rotated so that visual cue 460 is now in closer proximity to visual component 498. FIG. 4*c* shows that the perspective can be adjusted even further bring in visual cue 460 is even closer proximity to visual component 498. Thus, the player 300 may now improve their chances of getting the virtual golf boll 490 to rest near visual component 498 by aiming their golf shot at physical marker 220, which corresponds to visual cue 460.

It will be further understood that other visual components can be displayed to assist the player 300 in aiming. For example, in FIGS. 4*a*, 4*b* and 4*c*, a virtual tee box 499 is shown, which corresponds to the tee box 100, and a directional indicator 500 is displayed to indicate in what direction the virtual golf ball 490 will travel if the player 300 hits the golf ball 110 on a heading of 0 degrees (directly straight down the range surface 200).

Figure 3:
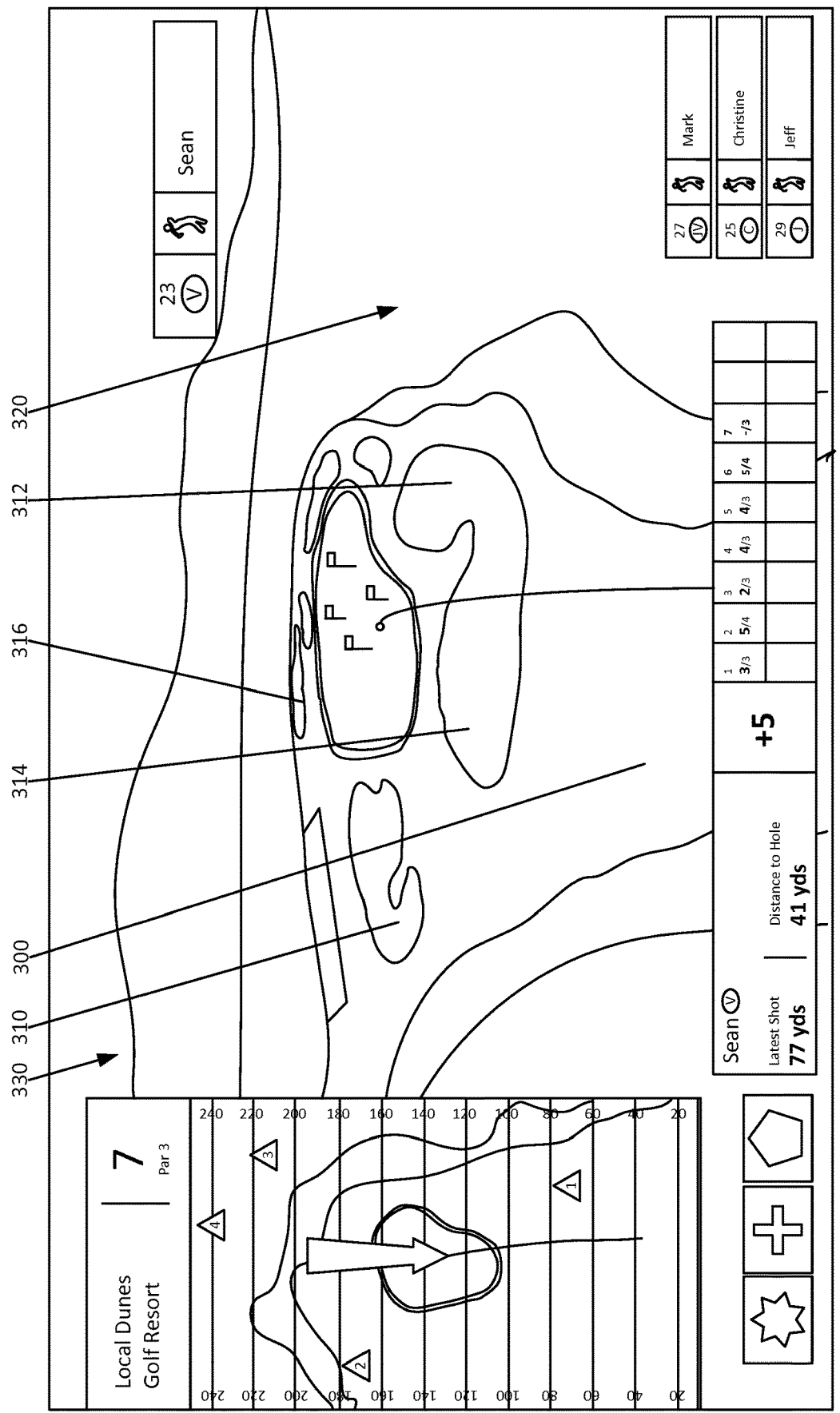
FIG. 3 depicts a front perspective view of a virtual environment.

It will be understood that other visual components appropriate to a golf game, if desired, may be used including without limitation fairways, sand traps, virtual tee boxes, water hazards, and out of bounds markers. In addition, it may be desirable to include other visual components to be depicted within the virtual environment that do not necessarily affect the play of the virtual golf game, but rather fill the background of the virtual environment, including without limitation, rivers, lakes, houses and other structures, mountains, trees, oceans, cliffs, clouds, and other weather-related constructs. FIG. 3 depicts another embodiment of the virtual environment depicted on the monitor 400, which includes a fairway [300], a plurality of sand traps 310, 312, 314, 316 an ocean 320, mountains 330, and other non-enumerated visual components.

Turning back to FIG. 1, the golf game begins by having the player 300 look at the monitor 400 to determine where they should aim their first golf shot. The virtual environment depicted on the monitor 400 will initially show the virtual golf ball 490 in a virtual tee box of a golf hole (corresponding to the actual golf ball 110 within the actual tee box 100). Depending on the particular shape and length of the fairway of the virtual golf hole depicted within the virtual environment, the player 300 will select a strategy to get his virtual golf ball into the cup on the green of the golf hole using the fewest golf shots. This strategy may involve selecting a particular golf club and striking the golf ball 110 in the tee box 100 thereby causing the golf ball 110 to fly through the air on a particular path onto the range surface 200. That path 495 will be depicted within the virtual environment and shown on the monitor 400. The monitor may then redraw the virtual environment to show the new position of the virtual golf ball 490. Play will continue with the player 300 iteratively targeting a desired physical marker, taking a golf shot, and then watching the monitor draw the path 495 of the virtual golf ball 490 that corresponds to the flight path of the actual golf ball 110 relative to the plurality of physical markers.

It is understood that the various embodiments of the game have different objectives and goals. The objective is to get the virtual golf ball 490 to the cup on the golf green 498 taking the fewest number of golf shots possible.

Figure 5:
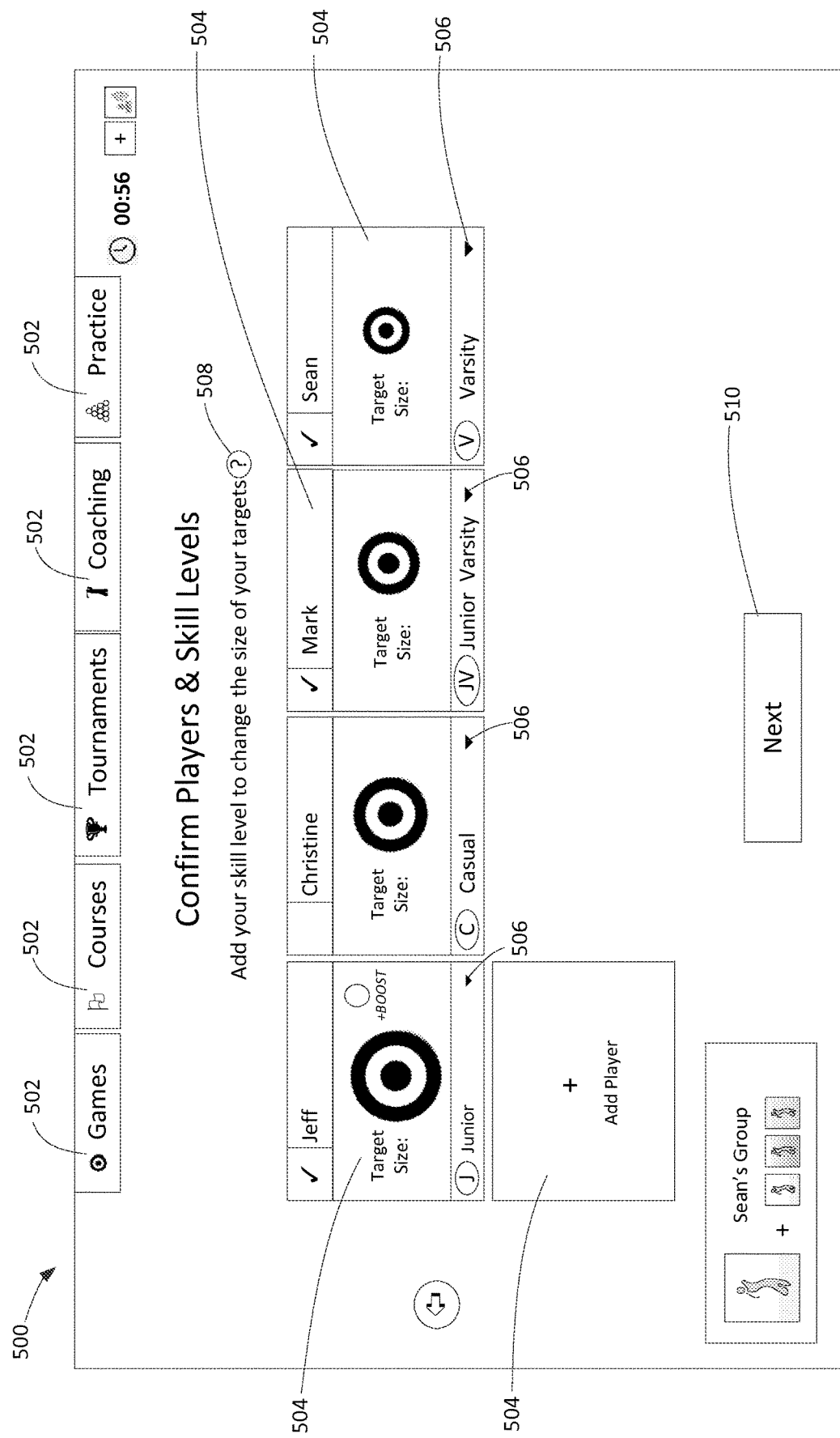
FIG. 5 depicts a game setup screen for a gaming system for use with the virtual environment.

Turning now to FIG. 5, depicted therein is a game setup screen 500 for a virtual golf game which may be depicted on the monitor 400. The game setup screen 500 may include a plurality of selectable menu items 502, a plurality of player boxes 504 each containing a drop-down menu 506 for selecting a skill level, a target size help menu 508 and a next button 510. The monitor 400 is a touch screen monitor; however, it will be understood that the monitor 400 could also use a mouse, track pad or be configured so that hand gestures or movements are detected.

The plurality of selectable menu items 502 allow a player of the virtual golf game to select the desired virtual environment they wish to encounter during their play time. Each of the virtual environments are displayed to the user on a screen or monitor and are imposed virtually onto the physical range, which allows the physical range to remain unchanged and present a variety of virtual environments to the player(s). The plurality of selectable menu items 502 may include, but is not limited to virtual golf games, courses, tournaments, coaching levels and practice environments.

Each of the selectable menu items 502 may include a variety of options which may be selected to determine the desired virtual environment. For example, the selectable menu item 502 entitled "Games" may include the virtual game of golf described above, card games such as 21 or poker, darts, long drive, HORSE, and the like. By way of further example, the selectable menu item 502 entitled "Courses" may include a list of golf courses with different environments and topography which may be selected. The selectable menu item 502 entitled "Tournaments" may include a list of various contests, or special instances of a game or golf course, in which there are a limited number of players or entries allowed, and within which players can earn rewards for earning the best score. The selectable menu item 502 entitled "Coaching" may provide a list of various coaching modules to select, such as distance training, use of various clubs, swing modification, etc. Also, the selectable menu item 502 entitled "Practice" may provide a list of practice courses, clubs, greens, distances and other variables which may be selected.

Figure 6:
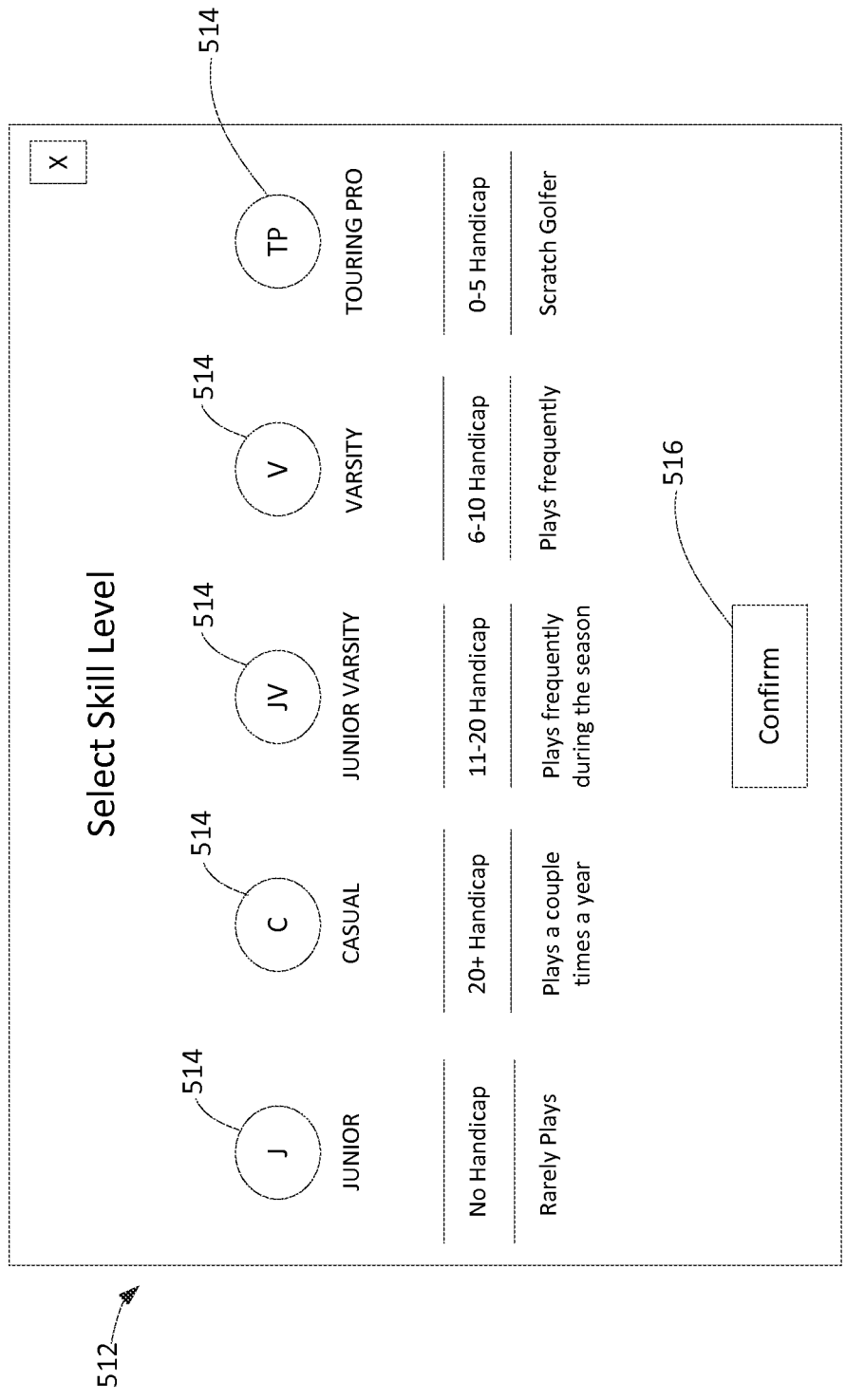
FIG. 6 depicts a skill select screen for selection of skill level within the gaming system.

The game setup screen 500 also allows additional players and player information to be added, deleted, or revised by selecting from the plurality of player boxes 504. Additionally, the skill level of a particular player may be added or changed by selecting the drop-down menu 506 associated with a particular player box 504. Referring to FIG. 6, shown therein is a skill level select screen 512 which is presented on the monitor 400 when the drop-down menu 506 associated with a particular player box 504 is selected. The skill level select screen 512 includes a plurality of skill levels 514 that may be associated with a particular player which may be selected. It will be understood by those skilled in the art that the selection of the appropriate skill level for a particular player can be based on a wide variety of skills, such as handicap, amount of playtime during a season, and other variables commonly used to determine skill level. Once the skill level is selected and the confirm button 516 pressed, the monitor 400 will present the game setup screen 500.

Figure 7A:
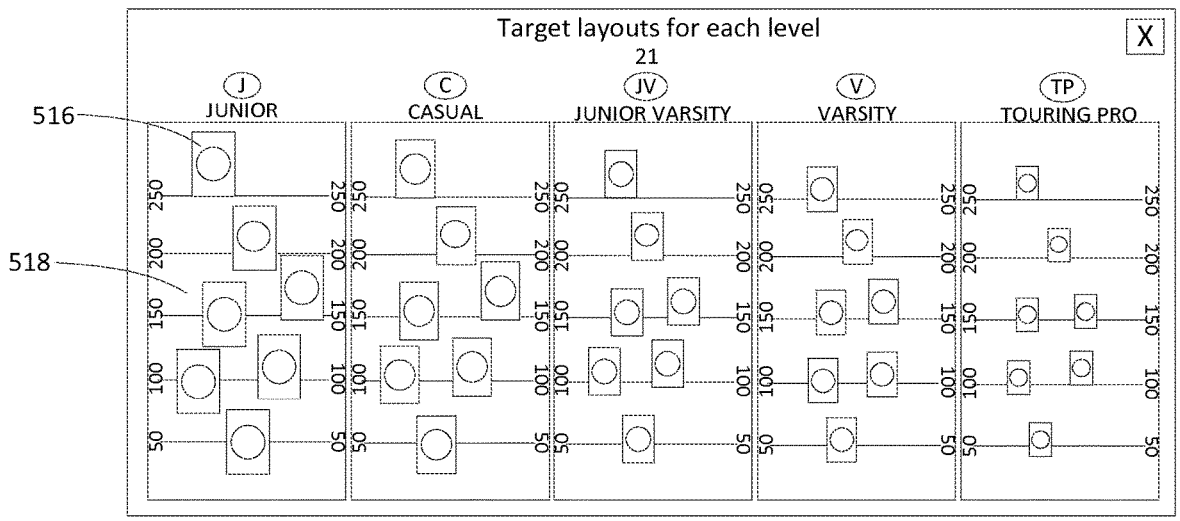
FIG. 7a depicts a target layout screen of a card game for each skill level within the gaming system.
Figure 7B:
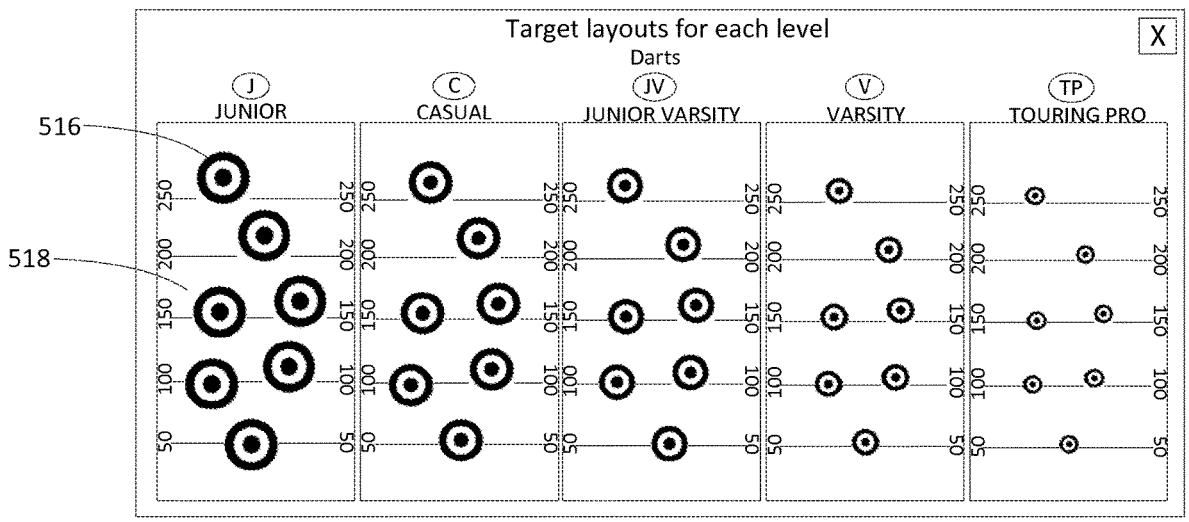
FIG. 7b depicts a target layout screen of a dart game for each skill level within the gaming system.
Figure 7C:
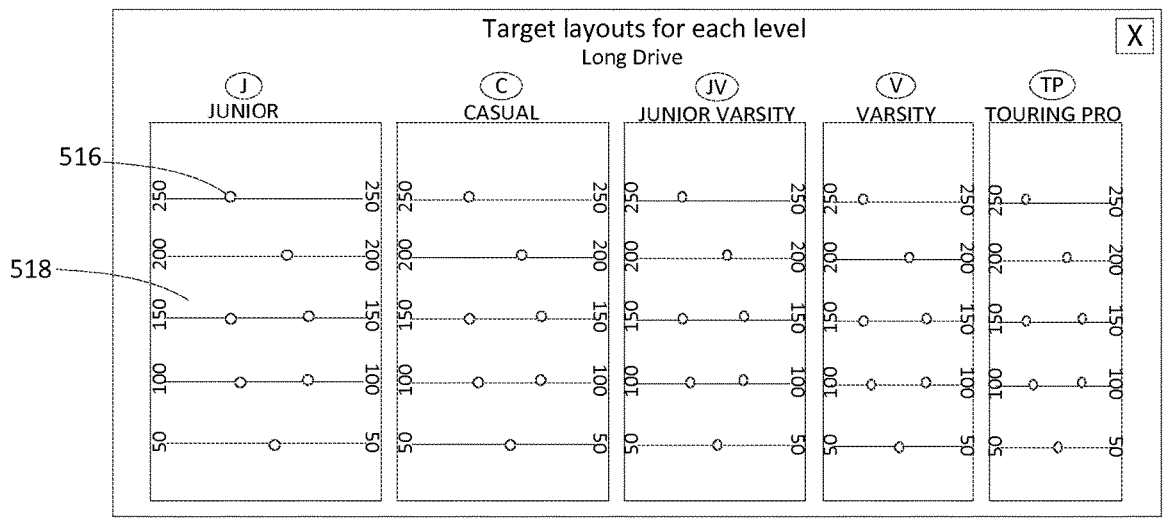
FIG. 7c depicts a target layout screen of a longest drive game for each skill level within the gaming system.

Turning to FIGS. 7a, 7b, and 7c, depicted therein are the various target layouts which are presented if the target size help menu 508 from the game setup screen 500 is selected. The target layouts are shown based on the game selected from the selectable menu items 502 and may show target layouts for a variety of virtual games. FIG. 7a shows a target layout for a virtual card game 21. FIG. 7b shows a target layout for a virtual dart game. FIG. 7c shows a target layout for a virtual long drive game. It will be understood that numerous other target layouts could be shown for the particular games included in the selectable menu items 502, including games such as poker, HORSE, or other games adapted to the virtual environment.

Each of the target layouts in FIGS. 7a, 7b, and 7c depicts the size of the targets 516 and/or the size of the in-bounds area 518 for the course depending on the skill level selected in the skill level menu 512 for each skill level. As further shown in FIGS. 7a and 7b, the size of the targets 516 may vary based on the skill level selected, such that a lower skill level presents the player with larger targets for the player to hit within the virtual game. Additionally, as shown in FIG. 7c, the size of the in-bounds area may also vary based on the skill level selected, such that a lower skill level presents the player with a larger in-bounds area 518. It will be understood that numerous combinations and sizes may be use for each of the targets 516 and/or in-bounds areas 518 depending on the type of game or desired settings for each game.

Figure 8A:
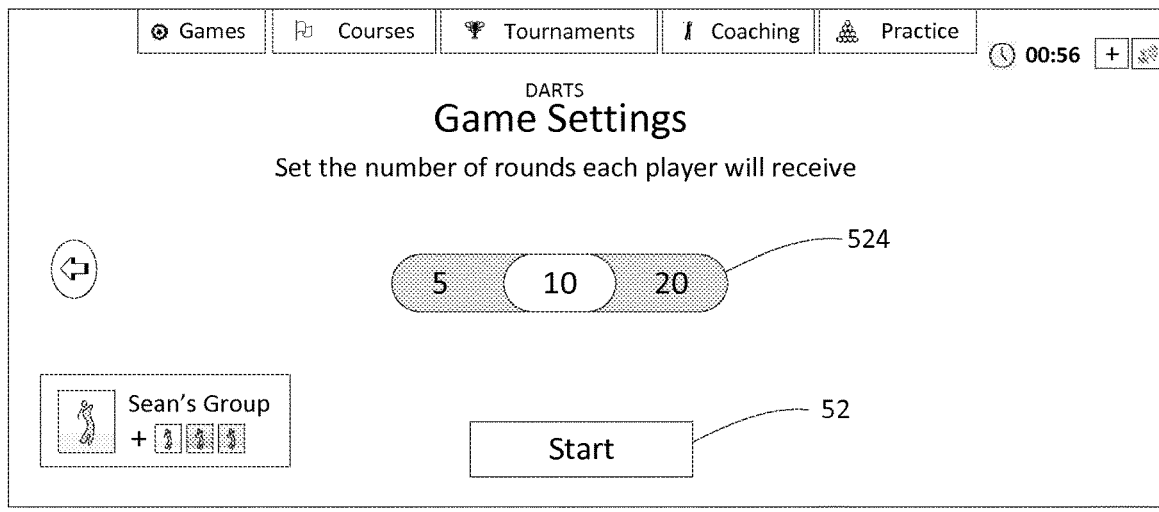
FIG. 8a depicts a game settings selection screen for a dart game.
Figure 8B:
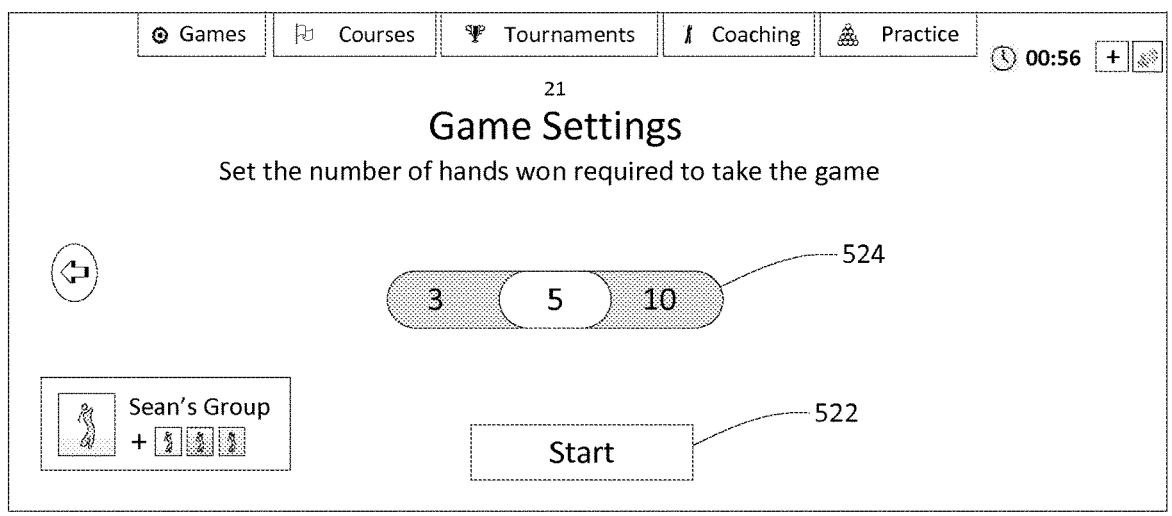
FIG. 8*b* depicts a game settings selection screen for a card game.
Figure 8C:
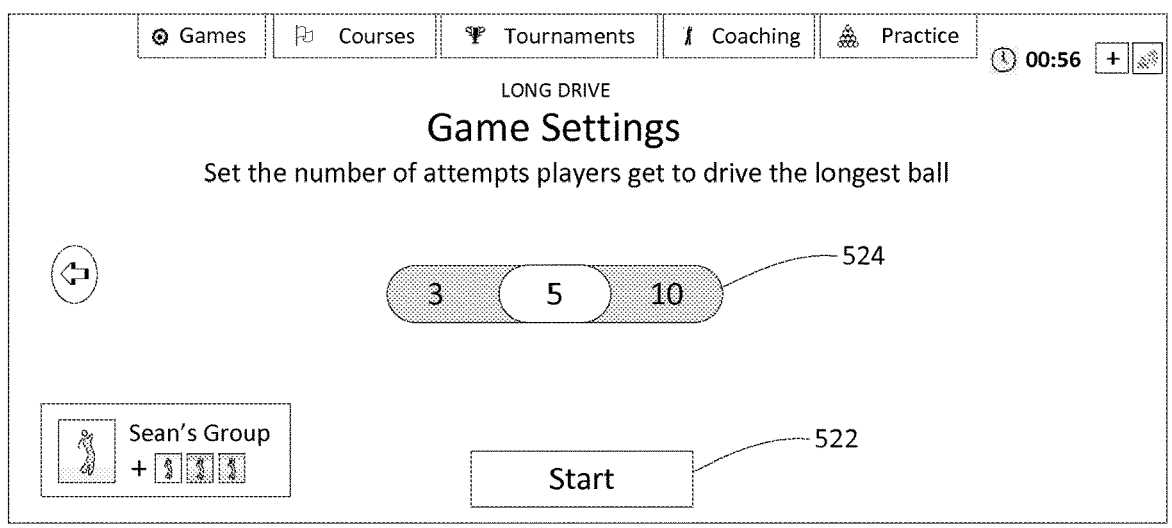
FIG. 8*c* depicts a game settings selection screen for a longest drive game.

When the next button 510 from the game setup screen 500 is pressed, and a particular game has been selected from the plurality of selectable menu items 502, the screen will display a new screen showing the game settings for the game selected. Turning to FIGS. 8a, 8b, and 8c, depicted therein are various game setting screens 520 for a particular game. The game setting screens 520 may include a start button 522 and a settings selection box 524 for selecting the various shots, length of the game, or attempts the player may receive during the virtual game.

Figure 9:
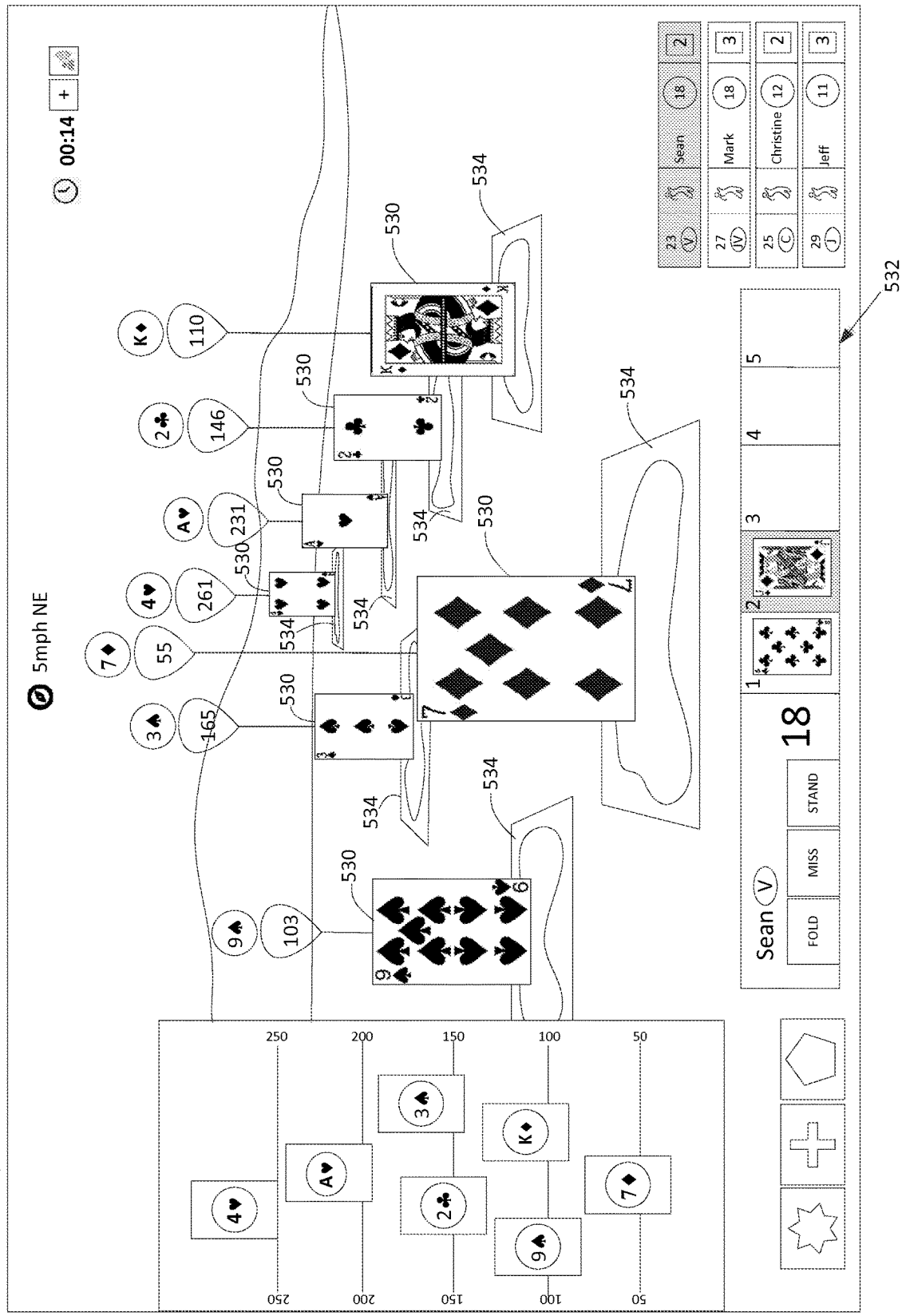
FIG. 9 depicts a front perspective view of a virtual environment for a card game.

Turning now to FIG. 9, depicted therein is a virtual environment for playing a blackjack card game. The virtual environment is displayed on the monitor 400. The virtual environment shown in FIG. 9 consists of a plurality of playing cards 530 and a player score card 532. The plurality of visual cards 530 are selected randomly from a pre-determined number of playing card decks with fifty-two (52) cards in each deal by a computer system and then assigned to various physical markers 534 within the virtual playing field. Although not depicted in FIG. 10, it will be understood that the playing field may also include an in-bounds and out-of-bounds area which may change size based on the skill level of the player. The player score card 532 shows the cards that have been hit by the player during each of that player's turns.

One or more players take turns trying to hit a particular playing card from the plurality of playing cards 540 with a sports ball to win the card or value assigned to the playing card. The players may take numerous turns to attempt to reach a certain total value, such as 21 for blackjack, or the values necessary to win 3 card or 5 card poker, etc. After all of the players have made the set number of attempts, the system resolves the players' resulting hands against each other based on the rules and hand hierarchy as required by the game and then announces the winner to be the player with the best hand. For example, in Blackjack, or 21, the player with the points total closest to 21 without going over 21 wins. Additionally, if there is a tie, the tied players may be allowed to take another turn to attempt to hit the highest value card on the virtual playing field. If a player does not hit a card during a turn, the player may have the opportunity to draw a card from the cards remaining in the deck, which is randomly assigned by the computer system. The probability of drawing a card helpful to that player's hand can be weighted such that a player of higher skill is more likely to draw a card that is unhelpful, while a player of lower skill is more likely to draw a card that is helpful based on the cards in the player's hand during that turn.

Figure 10:
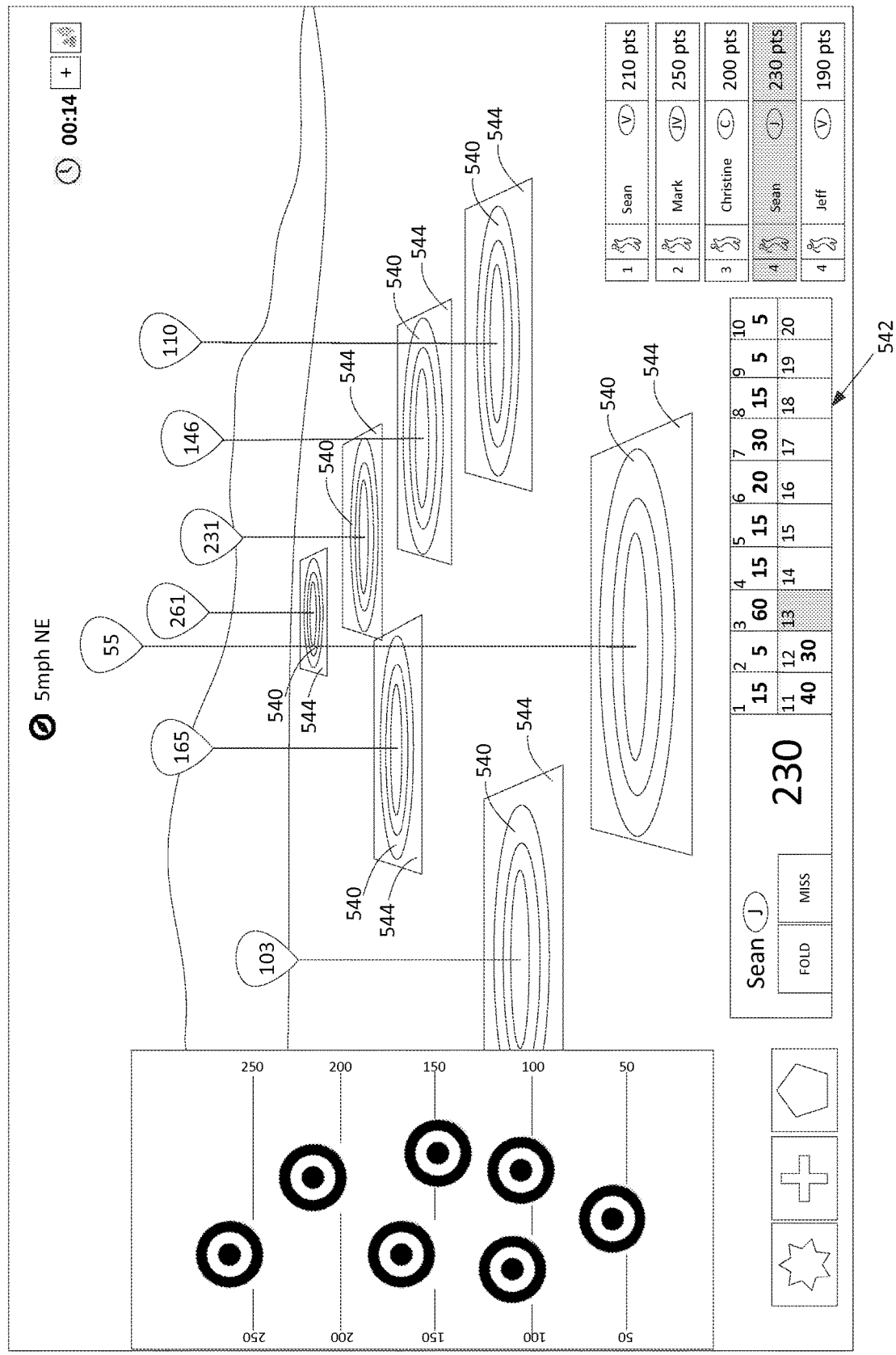
FIG. 10 depicts a front perspective view of a virtual environment for a dart game.

Turning now to FIG. 10, depicted therein is a virtual environment that is displayed on the monitor 400. The virtual environment is configured to play a game of darts. The virtual environment shown in FIG. 10 consists of a plurality of visual targets 540 and a player score card 542. The plurality of visual targets 540 are assigned to various physical markers 544 within the virtual playing field. It will be understood that although the visual targets 540 are shown as concentric rings, the visual targets 540 could be various shapes and sizes depending on the terrain of the selected target area or course. Further, although the physical markers 544 are depicted as rectangular in FIG. 10, it will be understood that the physical markers may be various shapes or not visible depending on the course selected. Although not depicted in FIG. 10, it will be understood that the playing field may also include an in-bounds and out-of-bounds area which may change size based on the skill level of the player. The player score card 542 shows the score that the player has earned during each round.

One or more players take turns trying to hit a particular target from the plurality of visual targets 540 with a sports ball to win the value assigned to that target and/or the rings around the target. After all of the players have made the set number of attempts, the system resolves each player's resulting scores against the other player's scores by summing the total number of points for each player. Additionally, if there is a tie, the tied players may be allowed to take another turn to attempt to hit the highest value target on the virtual playing field. If a player misses all of the targets during a turn, the player may be awarded a minimum number of points based on the skill level of the player.

Although the plurality of visual targets 540 are shown in two dimensions, such that they are lying flat on the playing surface area on the X-Y axis, it will be understood that the plurality of visual targets 540 could also be displayed in three dimensions similar to the plurality of playing cards 530 in FIG. 9, such that they are standing in the air on the X, Y and Z axis. Additionally, it will be understood that the plurality of playing cards 530 in FIG. 9 could also be displayed in two dimensions similar to the plurality of visual targets 540 in FIG. 10. Alternatively, the visual targets 540 could be projected onto a retention net that borders the range surface 200.

Although FIGS. 9 and 10 display specific games of blackjack and darts respectively, it will be understood that a variety of games could be displayed and played based on the games available in the computer system, including long drive, poker, HORSE, and numerous other options. For example, the game long drive is selected. The game is played so that each player takes turns trying to move the ball from that player's first position to the farthest possible position, wherein a farther landing place is equal to a higher point value. Each player takes a set number of attempts to advance the ball the farthest and the winner is the player whose final distance is the farthest away from the player's starting position. It will be understood that the size of the in-bounds and out-of-bounds area may change sizes based on the skill of the player such that players with higher levels of skills will be presented with a smaller in-bounds area than those of a lower skill level.

It will also be understood that although the virtual environment shown in FIGS. 9 and 10 are depicted on the monitor 400, the virtual environment could also be projected in front of the player, such as using a virtual reality display device, such as Google glass or other similar devices.

Figure 11:
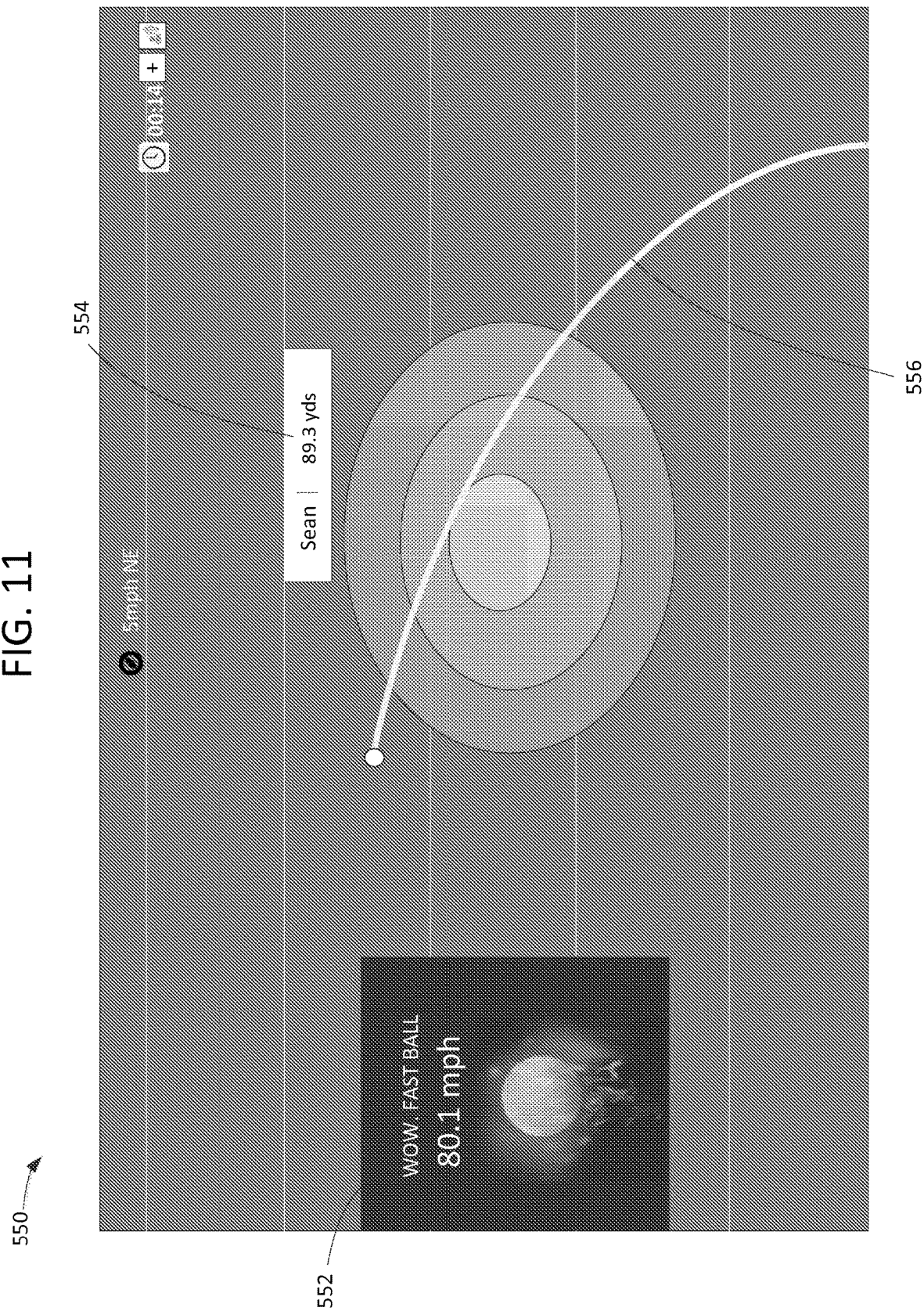
FIG. 11 depicts a screen shot of the flight path of an object and target within the virtual environment.

Turning to FIG. 11, depicted therein is a ball flight screen 550 that may be shown to the player on the monitor 400 during the flight of the ball and may also include information such as the speed of the ball 552, the exact location/distance 554 of the ball's landing and the flight path 556.

As used herein, the term "computer" may refer, but is not limited to a laptop or desktop computer, or a mobile device, such as a desktop, laptop, tablet, cellular phone, smart phone, personal media user (e.g., iPod), wearable computer, implantable computer, or the like. Such computing devices may operate using one or more operating systems, including, but not limited to, Windows, MacOS, Linux, Unix, iOS, Android, Chrome OS, Windows Mobile, Windows CE, Windows Phone OS, Blackberry OS, and the like.

As used herein, the term "mobile device" may refer, but is not limited to any computer, as defined herein, that is not fixed in one location. Examples of mobile devices include smart phones, personal media users, portable digital assistants, tablet computers, wearable computers, implanted computers, and laptop computers.

The system and method described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like, and preferably includes at least one tangible, non-transitory medium storing instructions executable to cause the system to perform functions described herein. Preferably, the computer-readable storage device includes a tangible, non-transitory medium. Such non-transitory media excludes, for example, transitory waves and signals. "Non-transitory memory" should be interpreted to exclude computer readable transmission media, such as signals, per se.

The systems and/or methods described herein, and steps thereof, may be realized in hardware, software or any combination of hardware and software suitable for a particular application. The hardware may include a general-purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine-readable medium.

The computer executable code may be created using a structured programming language such as C, an object oriented programming language such as .NET and C++, a lightweight data-interchange programming language such as JavaScript Object Notation (JSON) data-interchange format over HTTP POST request/response, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, each method described above and combinations thereof may be embodied in computer executable code that, when executing on one or more computing devices, performs the steps thereof. In another aspect, the processes may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not to be construed that there is only one of that element.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the instant disclosure may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

It should be noted that where reference is made herein to a method comprising two or more defined steps, the defined steps can be carried out in any order or simultaneously (except where context excludes that possibility), and the method can also include one or more other steps which are carried out before any of the defined steps, between two of the defined steps, or after all of the defined steps (except where context excludes that possibility).

Still further, additional aspects of the instant invention may be found in one or more appendices attached hereto and/or filed herewith, the disclosures of which are incorporated herein by reference as if fully set out at this point.

Thus, the invention is well adapted to carry out and attain the ends and advantages mentioned above as well as those inherent therein. While the inventive concept has been described and illustrated herein by reference to certain illustrative embodiments in relation to the drawings attached thereto, various changes and further modifications, apart from those shown or suggested herein, may be made therein by those of ordinary skill in the art, without departing from the spirit of the inventive concept the scope of which is to be determined by the following claims.

The invention claimed is:

1. A game-play environment, comprising:
a physical tee box (100) having a monitor (400);
a physical range surface (200) having a plurality of physical markers (210, 220, 230, 240); and a physical golf ball (110);
wherein the monitor (400) depicts a virtual environment (10) comprising:
  a virtual golf ball (490) corresponding to said physical golf ball (110);
  a plurality of visual cues (450, 460, 470, 480) corresponding to said plurality of physical markers (210, 220, 230, 240) of said range surface (200), wherein relative positions and distances between said plurality of physical markers (210, 220, 230, 240) are the same relative positions and distances depicted between said plurality of visual cues (450, 460, 470, 480);
  at least one visual component that does not correspond to said physical markers (210, 220, 230, 240) of said range surface (200); and
  a virtual golf ball flight path (495) corresponding to an actual flight path of said physical golf ball (110) from said tee box (100) onto said range surface (200);
  wherein said virtual environment (10) is configured to redraw the virtual environment after a flight of the physical golf ball (110) to show a new position of the virtual golf ball (490) defined by the corresponding virtual golf ball flight path (495), and to allow a player to play a virtual golf hole by iteratively performing a sequence of targeting a desired physical marker, taking a golf shot, and watching the monitor (400) draw the virtual golf ball flight path (495) that corresponds to the flight path of said physical golf ball (110) from said tee box (100) onto said range surface (200).

2. The game-play environment of claim 1 wherein the (400) monitor depicts a virtual final resting place of the virtual golf ball (490) corresponding to a relative position and distance from each of said plurality of visual cues (450, 460, 470, 480) that correspond to a relative position and distance of said physical golf ball (110) from each of said plurality of physical markers (210, 220, 230, 240) of said range surface (200).

3. The game-play environment of claim 1 wherein the at least one visual component that does not correspond to said physical markers (210, 220, 230, 240) comprises a virtual golf hole.

4. The game-play environment of claim 3 wherein the at least one visual component that does not correspond to said physical markers (210, 220, 230, 240) further comprises a virtual golf green, a virtual golf fairway, a virtual directional indicator, a virtual sand trap, a virtual water hazard, a virtual out of bounds marker, a virtual background feature, or a combination thereof.

5. The game-play environment of claim 1 wherein said game-play environment is configured to selectively rotate the depiction of the plurality of visual cues relative to the plurality of visual components so that a visual cue in the plurality of visual cues is depicted in closer proximity to a visual component within the plurality of visual components.

6. The game-play environment of claim 1 wherein the at least one visual component comprises a playing card, a dart board, a concentric ring, or a combination thereof.

7. The game-play environment of claim 6 wherein said virtual environment is configured to change a target size of the at least one visual component based on a selected player skill level.

8. The game-play environment of claim 1 wherein said game-play environment is configured to selectively adjust the depiction of the virtual environment (10) so that said plurality of visual cues (450, 460, 470, 480) that correspond to the plurality of physical markers (210, 220, 230, 240) are depicted in alignment with the desired visual components.

9. A method of providing a game using a game-play environment, the game-play environment comprising:
  a physical tee box (100) having a monitor (400);
  a physical range surface (200) having a plurality of physical markers (210, 220, 230, 240); and
  a physical golf ball (110); the method comprising the steps of:
  depicting, on the monitor (400), a virtual environment (10), the virtual environment (10) comprising:
    a virtual golf ball (490) corresponding to said physical golf ball (110);
    a plurality of visual cues (450, 460, 470, 480) corresponding with the physical markers (210, 220, 230, 240) on the range surface (200); wherein the relative positions and distances between the physical markers (210, 220, 230, 240) are the same relative positions and distances depicted between the visual cues (450, 460, 470, 480);
    at least one visual component that does not correspond to said physical markers (210, 220, 230, 240) of said range surface (200);
    a virtual golf ball flight path (495) corresponding to an actual flight path of said physical golf ball (110) from said tee box (100) onto said range surface (200);
  redrawing the virtual environment, on the monitor (400) after a flight of the physical golf ball (110) to show a new position of the virtual golf ball (490) defined by the corresponding virtual golf ball flight path (495); and
  allowing a player to play a virtual golf hole by iteratively performing a sequence of targeting a desired physical marker, taking a golf shot, and watching the monitor (400) draw the virtual golf ball flight path (495) that corresponds to the flight path of said physical golf ball (110) from said tee box (100) onto said range surface (200).

10. The method of claim 9 further comprising the step of depicting, within the virtual environment on the monitor (400), a virtual final resting place of the virtual golf ball (490) corresponding to a relative position and distance from each of said plurality of visual cues (450, 460, 470, 480) that correspond to a relative position and distance of said physical golf ball (110) from each of said plurality of physical markers (210, 220, 230, 240) of said range surface (200).

11. The method of claim 10 further comprising the step depicting, within the virtual environment on the monitor (400), an actual flight path of the physical golf ball (110) as it travels from the physical tee box (100) through the air and onto the physical range surface (200).

12. The method of claim 9 further comprising the step of depicting, within the virtual environment on the monitor (400), at least one of the plurality of visual components that does not correspond to the physical markers (210, 220, 230, 240) comprises a virtual golf hole.

13. The method of claim 12 wherein the at least one visual component that does not correspond to said physical markers (210, 220, 230, 240) further comprises a virtual golf green, a virtual golf fairway, a virtual directional indicator, a virtual sand trap, a virtual water hazard, a virtual out of bounds marker, a virtual background feature, or a combination thereof.

14. The method of claim 9 further comprising the step of selectively rotating the depiction of the plurality of visual cues (450, 460, 470, 480) relative to the plurality of visual components so that a visual cue in the plurality of visual cues (450, 460, 470, 480) is depicted in closer proximity to a visual component within the plurality of visual components.

15. The method of claim 9 wherein at least one of the visual components that does not correspond to said physical markers (210, 220, 230, 240) further comprises a playing card, a dart board, a concentric ring, or a combination thereof.

16. The method of claim 15 wherein said virtual environment is configured to change a target size of the at least one visual component based on an associated player skill level.

17. The method of claim 9 further comprising the step of selectively adjusting the depiction of the virtual environment (10) so that said plurality of visual cues (450, 460, 470, 480) that correspond to the plurality of physical markers (210, 220, 230, 240) are depicted in alignment with the desired visual components.

18. A virtual game-play environment, comprising:
- a virtual golf ball (490) corresponding to a physical golf ball (110);
- a plurality of visual cues (450, 460, 470, 480) corresponding to a plurality of physical markers (210, 220, 230, 240) of said range surface (200), wherein relative positions and distances between said plurality of physical markers (210, 220, 230, 240) are the same relative positions and distances depicted between said plurality of visual cues (450, 460, 470, 480);
- at least one visual component that does not correspond to said physical markers (210, 220, 230, 240) of said range surface (200); and
- a virtual golf ball flight path (495) corresponding to an actual flight path of said physical golf ball (110) from said tee box (100) onto said range surface (200);
- wherein said virtual game-play environment (10) is configured to redraw the virtual game-play environment after a flight of the physical golf ball (110) to show a new position of the virtual golf ball (490) defined by the corresponding virtual golf ball flight path (495), and to allow a player to play a virtual golf hole by iteratively performing a sequence of targeting a desired physical marker, taking a golf shot, and watching the monitor (400) draw the virtual golf ball flight path (495) that corresponds to the flight path of said physical golf ball (110) from said tee box (100) onto said range surface (200).

19. The virtual game-play environment of claim 18 wherein the virtual game-play environment (10) depicts a virtual final resting place of the virtual golf ball (490) corresponding to a relative position and distance from each of said plurality of visual cues (450, 460, 470, 480) that correspond to a relative position and distance of said physical golf ball (110) from each of said plurality of physical markers (210, 220, 230, 240) of said range surface (200).

20. The virtual game-play environment of claim 18 wherein the at least one visual component that does not correspond to said physical markers (210, 220, 230, 240) comprises a virtual golf hole.

21. The virtual game-play environment of claim 20 wherein the at least one visual component that does not correspond to said physical markers (210, 220, 230, 240) further comprises a virtual golf green, a virtual golf fairway, a virtual directional indicator, a virtual sand trap, a virtual water hazard, a virtual out of bounds marker, a virtual background feature, or a combination thereof.

22. The virtual game-play environment of any claim 18 wherein said virtual game-play environment is configured to selectively rotate the depiction of the plurality of visual cues relative to the plurality of visual components so that a visual cue in the plurality of visual cues is depicted in closer proximity to a visual component within the plurality of visual components.

23. The virtual game-play environment of claim 18 wherein the at least one visual component comprises a playing card, a dart board, a concentric ring, or a combination thereof.

24. The virtual game-play environment of claim 23 wherein said virtual game-play environment is configured to change a target size of the at least one visual component based on an associated player skill level.

25. The virtual game-play environment of claim 18 wherein said virtual game-play environment is configured to selectively adjust the depiction of the virtual environment (10) so that said plurality of visual cues (450, 460, 470, 480) that correspond to the plurality of physical markers (210, 220, 230, 240) are depicted in alignment with the desired visual components.

* * * * *